United States Patent [19]
Stoop et al.

[11] Patent Number: 5,350,409
[45] Date of Patent: Sep. 27, 1994

[54] RATE ADAPTIVE PACEMAKER WITH ADJUSTMENT OF SENSOR RATE AS A FUNCTION OF SENSED SINUS RATE

[75] Inventors: Gustaaf A. Stoop, Dieren; Malcolm J. S. Begemann, Velp; Johannes van der Veen; Marcus O. Filipovich, both of Arnhem, all of Netherlands

[73] Assignee: Vitatron Medical, B.V., Dieren, Netherlands

[21] Appl. No.: 49,181

[22] Filed: Apr. 19, 1993

[51] Int. Cl.$^5$ ............................................. A61N 1/365
[52] U.S. Cl. ....................................................... 607/17
[58] Field of Search ................................. 607/9, 17–22

[56] References Cited

U.S. PATENT DOCUMENTS

| | | | |
|---|---|---|---|
| 4,313,442 | 2/1982 | Knudson et al. | 607/17 |
| 4,527,568 | 7/1985 | Rickards | 128/419 PG |
| 4,855,524 | 8/1989 | Baker, Jr. | 607/17 |
| 4,856,523 | 8/1989 | Sholder et al. | 128/419 PG |
| 4,860,751 | 8/1989 | Callaghan | 607/20 |
| 4,867,162 | 9/1989 | Schaldach | 128/419 PG |
| 4,966,146 | 10/1990 | Webb et al. | 128/419 PG |
| 5,052,388 | 10/1991 | Sivula et al. | 128/419 PG |
| 5,065,759 | 11/1991 | Begemann et al. | 128/419 PG |
| 5,085,215 | 2/1992 | Nappholz et al. | 607/21 |
| 5,133,349 | 7/1992 | Heinze | 607/22 |

OTHER PUBLICATIONS

"Description of the Diamond ™ Model 800 Pacemaker For Pilot Study Clinical Investigators," F. van Krieken and G. Stoop, unpublished confidential document; front page and p. 23.

*Primary Examiner*—William E. Kamm
*Attorney, Agent, or Firm*—Woodcock Washburn Kurtz Mackiewicz & Norris

[57] ABSTRACT

A rate adaptive pacemaker and method of operation, where the sensor-indicated rate is adjusted as a function of sensed sinus rate. The pacemaker is particularly adapted for VDDR operation. The natural sinus rate is compared to the sensor-indicated rate at one or more rates, and the sensor response function is adjusted, or adapted as a function of such comparisons, so as to optimize sensing of the atrial rate and maintenance of synchronous operation. The rate response function may be adjusted specifically at upper pacing limit, and may also be adjusted as a function of comparisons made at other rates.

19 Claims, 3 Drawing Sheets

RATE ADAPTIVE PACEMAKER WITH ADJUSTMENT OF SENSOR RATE AS A FUNCTION OF SENSED SINUS RATE

BACKGROUND OF THE INVENTION

1. Field of the Invention

This invention lies in the area of rate responsive cardiac pacemakers and the method of operation of same and, more particularly, dual chamber rate responsive pacemaker systems with means for adjusting the rate response relative to the sensed natural sinus rate so as to optimize tracking of the natural sinus rate as long as it is reliable.

2. Description of the Prior Art

Dual chamber rate responsive pacemakers are now widely available from pacemaker manufacturers. Such pacemakers may be of many types, including the types designated as DDDR or VDDR. The DDDR pacemaker paces and senses in both chambers, i.e., both the atrium and the ventricle, and has rate responsive (R) backup to provide pacing in the absence of sensed natural beats, or to provide rate responsive ventricular pacing during atrial tachyarrhythmias in the absence of natural ventricular beats. The DDDR pacemaker has a lead that is placed within the atrium to deliver atrial pace pulses, as well as to sense natural atrial (sinus) signals, and a ventricular lead for pacing and sensing in the ventricle. In contrast, the VDDR pacemaker paces only in the ventricle, although it senses in both the atrium and the ventricle. The VDDR pacemaker system may be made simpler by incorporating a single lead, which has a floating atrial electrode for sensing atrial signals, in a known manner. The VDDR pacemaker is indicated for patients who are determined to have a good and reliable sinus rate, so that for a good bit of the anticipated lifetime of the patient, natural atrial signals will be present from which ventricular pace pulses can be tracked, thereby providing synchronized pacing.

Particularly with respect to the VDDR pacemaker, it is seen that there is an inherent desirability of maximizing use of the sinus rate, i.e., avoiding takeover of the pacing function as long as a good atrial signal is present and sensed. For a rate responsive pacemaker, this leads to the desirability of correlating the rate response as closely as possible to the sensed natural sinus, while still enabling the rate response to take over pacing control when and if the sinus does not accurately reflect cardiac demand. Thus, for example, if a patient develops chronotropic incompetence after implant of a VDDR pacemaker, there must be an ability to switch modes or otherwise enable the sensor response to override the sinus.

The prior art indicates many schemes for adjusting rate response as a function of exercise. Such schemes include algorithms for ramping up rate upon the onset of exercise, and ramping down rate after exercise, so as to provide a more physiologically natural response to exercise. Such pacemaker systems thus involve predetermined programming for optimizing the pacing response in terms of known optimum responses. It is also known to adjust the rate response as a function of a separate sensor, and to switch to the rate response mode if the atrial rate looks to be unreliable. See, for example, U.S. Pat. No. 4,527,568, Rickards, assigned to the same assignee as this invention, where atrial and sensor rate are compared, and the sensor takes over if conditions indicate that this is desirable. However, in pacemakers to date, there is no capability of enabling the rate response function (or algorithm) to track or adapt to the actual sinus rate. Particularly for VDDR mode pacers there is a need to provide a rate response control wherein the sensor-indicated pacing rate is correlated to and tracks just below the sinus rate, so as to optimize sensing of the atrial rate and provide for pacing takeover only when the sinus is unreliable (e.g., atrial tachyarrhythmias) or missing.

SUMMARY OF THE INVENTION

In view of the prior art needs as stated above, it is an object of this invention to provide a rate adaptive pacemaker with the capability of adjusting the sensor/rate relation as a function of sensed sinus rate, particularly for a pacemaker which operates in the VDDR mode. The aim of the improved pacemaker of this invention is to provide a rate response which follows the sensed sinus rate, i.e., the correlation between sensor-indicated pacing rate (R) and the sensor input is adjusted by ongoing comparisons of sinus rate and sensor rate.

In accordance with the above object, there is provided a rate responsive demand pacemaker, and method of operating same, wherein the sensor-derived rate response is adapted at one or more rates through the pacing range by comparing a measure of the natural sinus rate and the rate response rate (R), and adjusting the response function as a function of that comparison. The comparison may appropriately be made at preselected rates, including the upper pacing limit (UPL) and other rates throughout the pacemaker pacing range. In order to guard against too fast an adjustment of the response function, a limit is provided for limiting the amount and frequency of such adjustments to the rate response function.

DESCRIPTION OF THE PREFERRED EMBODIMENTS

Reference is made to U.S. Pat. No. 5,247,930, titled "Dual Chamber Pacing System With Dynamic Physiological Tracking and Optimized Synchronous Pacing," assigned to the same assignee. This patent, which is incorporated herein by reference, discloses a dual chamber pacemaker operable in a DDDR or VDDR mode, and is background for the present invention. The specification of U.S. Pat. No. 5,247,930 defines a physiological rate, or "phys rate" which is a measure of sensed atrial rate. As defined in the referenced case, such phys rate tracks the sensed sinus rate, but does not include sensed beats which appear to be non-physiological. In this specification as follows, and the claims appended hereto, the terms "sinus rate" or "atrial rate," as well as the term "measure of the sensed atrial rate," are used. Reference is also made to U.S. Pat. No. 5,065,759, Begemann et at., issued Nov. 19, 1991 and assigned to the same assignee as this application, which patent is hereby incorporated by reference. The referenced patent discloses a rate responsive pacemaker using two sensors to obtain a combined or optimum rate response. As used herein, the term "sensor" may refer to one or more sensors used for detecting signals (S) from which an indicated pacing rate (R) may be derived. Also, in the following description of the embodiments of this invention, reference to the response curve or slope may mean either the correlation curve of a single sensor, or may refer to the response of combined sensors. The more general term "rate response" or "rate response function" is used to indicate the overall correlation of pacing rate (R) as indicated by the sensor input (S). Reference is made to U.S. Pat. No. 5,065,759, for examples of QT and activity "curves," as well as a combined response.

Figure 1:
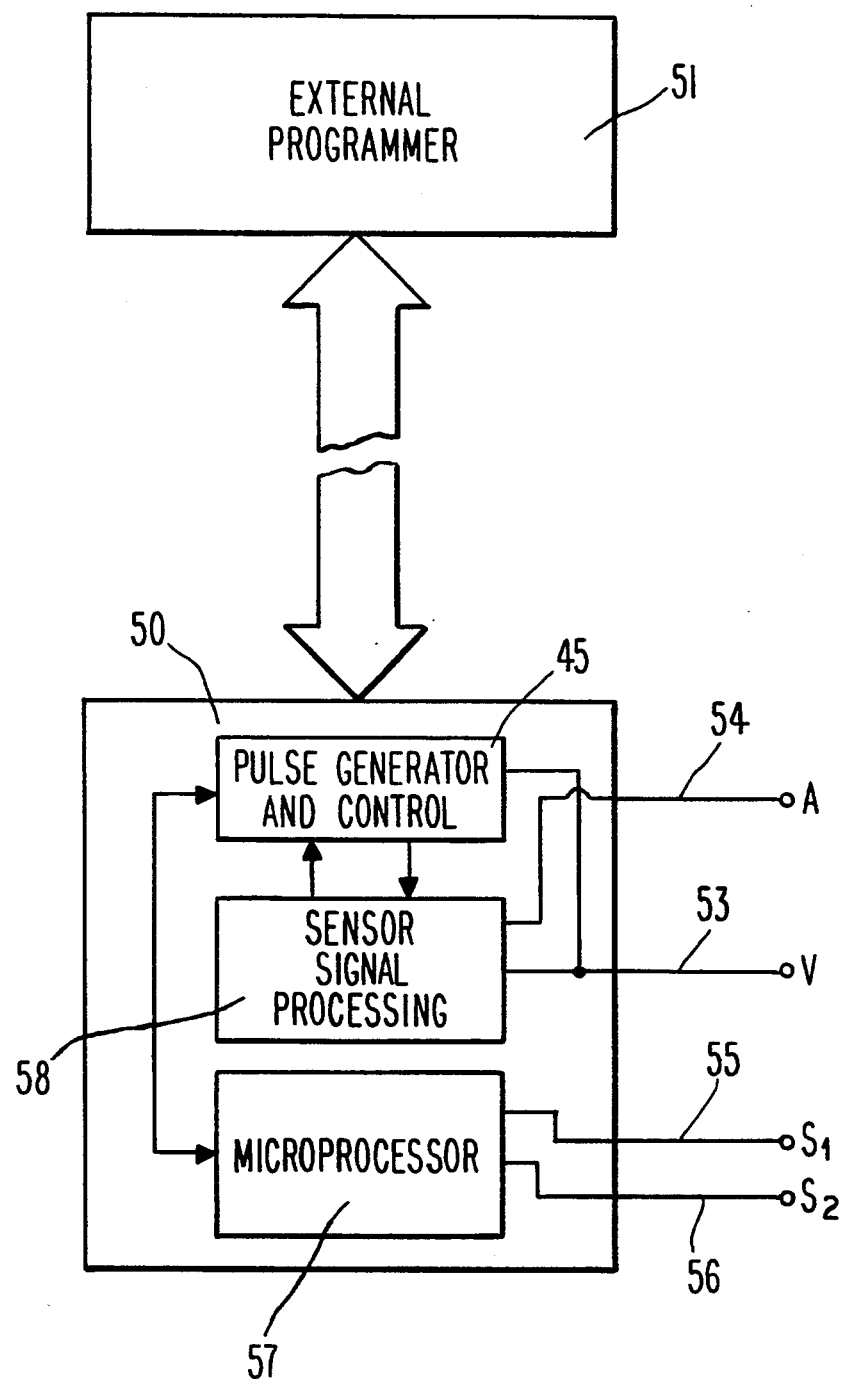
FIG. 1 is a block diagram of basic components of a pacemaker in accordance with this invention.

Referring now to FIG. 1, there is shown a schematic representation of a pacer system as utilized in this invention. A pacemaker, preferably an implantable pacemaker 50, is used with an external programmer 51, the external programmer operating in a known manner to program pacemaker variables. A lead 53 is illustrated as connecting to the ventricle, such lead delivering stimulus pulses to the ventricle and also providing sensed patient heartbeat signals to the pacemaker in a known manner. A lead 54 is illustrated as connecting the pacemaker to the atrium. In a DDDR pacemaker, lead 54 both delivers atrial stimulus pulses and provides sensed atrial signals back to the pacemaker. As is understood, for a VDDR pacemaker, a single lead is used, and the sensing electrode on lead 54 is in fact a floating electrode on the same lead as extends into the ventricle. Leads 55 and 56 are shown connected to sensors S1 and S2 in a patient, for providing rate responsive control parameters. For a system using the QT interval as a parameter, no separate sensor is required since the ventricular pacing electrode senses the QRS-T complex.. The pacemaker is illustrated as having a microprocessor 57, which includes memory for carrying the software of the algorithm of this invention. A block 58 is also indicated for signal processing of signals derived from the leads 53, 54 and sensors S1, S2 in a known manner. The pacemaker further contains conventional means 45 for generating stimulus pulses, inhibiting on demand, controlling pulse rate, sensing QRS and T wave portions, etc. Also, it is known in the art that in a pacing system which uses QT interval as a rate-indicating parameter, the sensor rate (R) may be obtained during the presence of natural beats by periodically and temporarily overriding the natural rate to deliver pace pulses and thereby determine the Q-T interval.

It is further to be noted that the invention is explained by reference to rate. As is well known, interval is the inverse of rate, i.e., pacing interval is the inverse of pacing rate. Thus, it is understood that the invention can be implemented equally with reference to the interval domain, i.e., whereby the pacing interval is controlled by sensors and/or an average atrial interval is determined instead of rate. Thus, rate and interval are understood to be interchangeable in defining the scope of the invention.

Figure 2A:
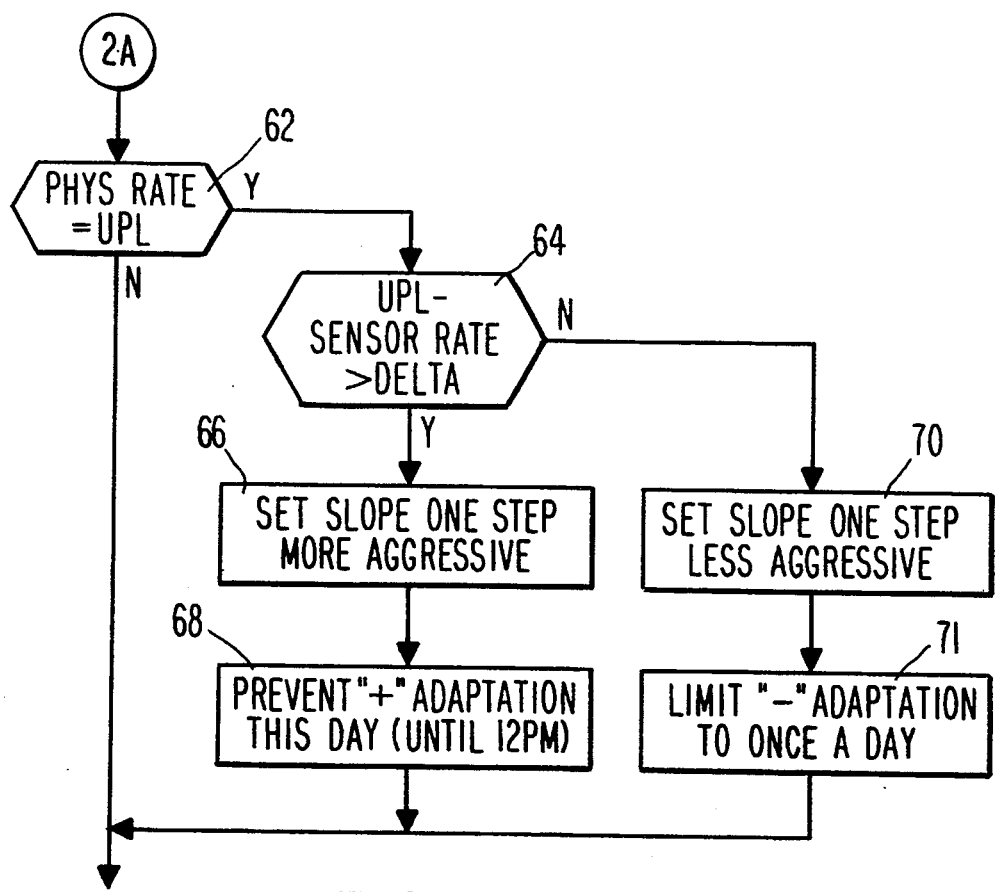
FIG. 2A is a flow diagram illustrating the steps carried out for changing the rate response function at UPL when the sinus rate is determined to be equal to the pacemaker upper pace limit (UPL).

Referring now to FIG. 2A, there is shown a simplified flow diagram for adaptation of the rate response slope at UPL, when phys rate reaches UPL. By positive adaptation it is meant that the slope of the rate response curve is adapted, or adjusted so as to more quickly bring pacing rate to UPL, i.e., make the rate response more aggressive in responding to exercise or other demand for increased heart rate. Conversely, negative adaptation means adjusting the response function so that pacing rate is brought up to UPL more slowly, or less aggressively. At block 62, it is determined whether phys rate is equal to UPL. Phys rate is a measure of sensed atrial rate, or sinus rate, in accordance with U.S. Pat. No. 5,247,930. If the answer is no, this subroutine is exited, as no adaptation is called for. However, if the answer is yes, the routine goes to 64, where the difference between UPL and the sensor rate is determined, and compared to a predetermined value delta. The purpose of this logic step is to determine whether the sensor rate is sufficiently far below UPL such that it is pot calling for a high enough rate. If the answer is yes, the routine branches to block 66, where the response slope is set to be one step more aggressive. Thus, by making the slope at UPL bring pacing rate up to UPL faster, i.e., more aggressively, the rate response is adjusted to better correspond to the condition where sinus rate equals UPL. Following this, at block 68, the pacemaker takes logical steps to prevent further positive adaptation during this clocked day, e.g., until 12 p.m. This may be done, for example, by setting a prevent flag before block 62 which would prevent entering this routine until the pacemaker internal clock indicates that another day has arrived, in which case the prevent flag is reset. Alternately, if the comparison at 64 produces a no response, the routine branches to block 70, where the slope is set to be one step less aggressive. Note that the steps taken in block 66 and 70 may be the same, or they may be slightly different to introduce some hysteresis in the adaptation of procedure. Following the step change in slope at block 70, the routine goes to block 71 where it limits negative adaptation to once a day, i.e., sets a flag to prevent any further negative adaptation until the next day. In a refinement of the routine of FIG. 2A, step 70 may be preceded with a block that determines when (UPL-Sensor Rate) <delta B, and followed by a block which prevents further negative adaptation until the rate drops delta C below UPL, where delta B and delta C are predetermined rate differentials. By this further variation, there is added the feature that no adaptation takes place if the sensor rate lies in the proper range, i.e., UPL-sensor rate is between delta and delta B.

Figure 2B:
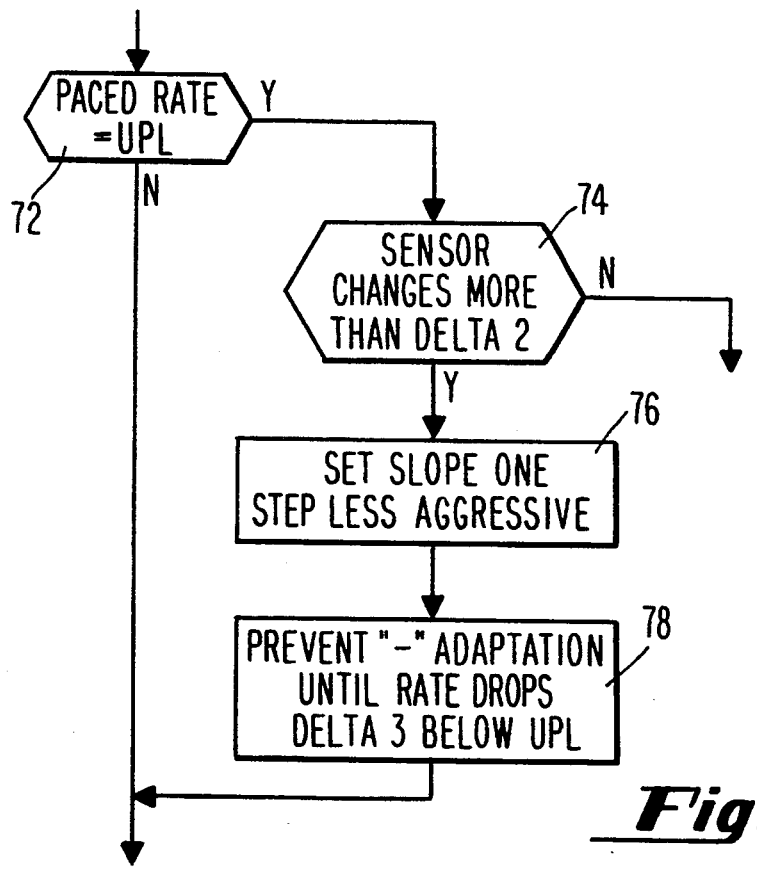
FIG. 2B is flow diagram indicating the steps taken by the pacemaker of this invention in adapting the rate response function when paced rate is determined to be equal to UPL.

Referring now to FIG. 2B, there is a simplified block diagram of a routine carried out by the pacemaker of this invention, for introducing negative adaptation of the rate response at UPL. This routine is entered during pacing as shown at block 72, where it is determined whether the paced rate, i.e., R, is equal to UPL during pacing. If the answer is no, the routine exits. However, if the answer is yes. the routine branches to block 74, where the pacemaker determines whether the sensor value (S) has changed more than a predetermined interval, designated delta 2. Specifically, the pacer stores the sensor value when the pacing rate (R) initially reaches UPL ($S_i$). Each cycle thereafter, until R falls delta 3 below UPL, the pacemaker compares S with $S_i$ to see if S has increased more than delta 2. If the sensor value does not change by the predetermined increment, the routine exits. However, if it does change, this indicates that the rate response was overly aggressive, i.e., pacing rate reached UPL before the patient had reached the point of exercise calling for maximum pacing rate. Correspondingly, if this condition is met, the routine branches to block 76, where the slope is set to be one step less aggressive, i.e., the slope is changed in the direction such that R does not reach UPL as quickly. Following this, the routine goes to block 78, where a prevent step is taken, similar to block 68, to prevent any additional negative adaptation until the rate (R) drops the predetermined amount, delta 3, below UPL. Note that in this embodiment, the slope at URL is only set more aggressively if the pacemaker senses that the sinus rate response, e.g., to exercise, is more aggressive.

Figure 3:
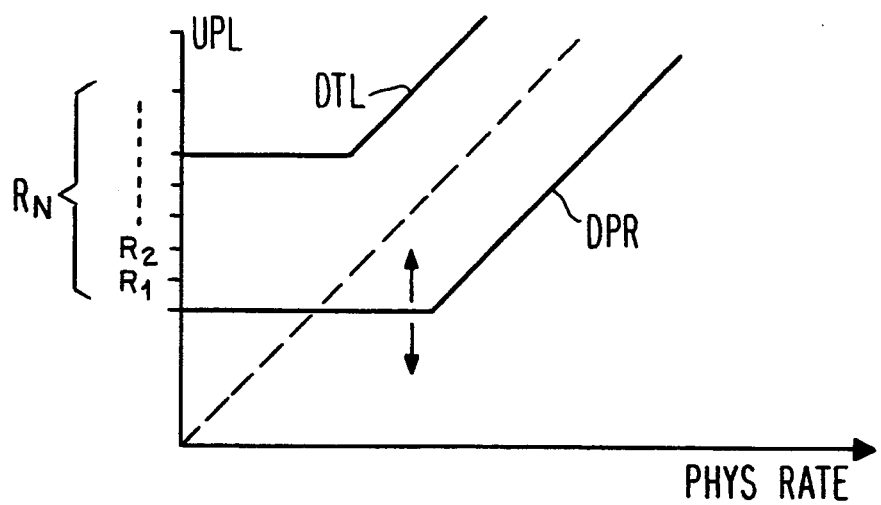
FIG. 3 is a graph showing decision curves and the effect thereon of changes in sensor rate (R).
Figure 4:
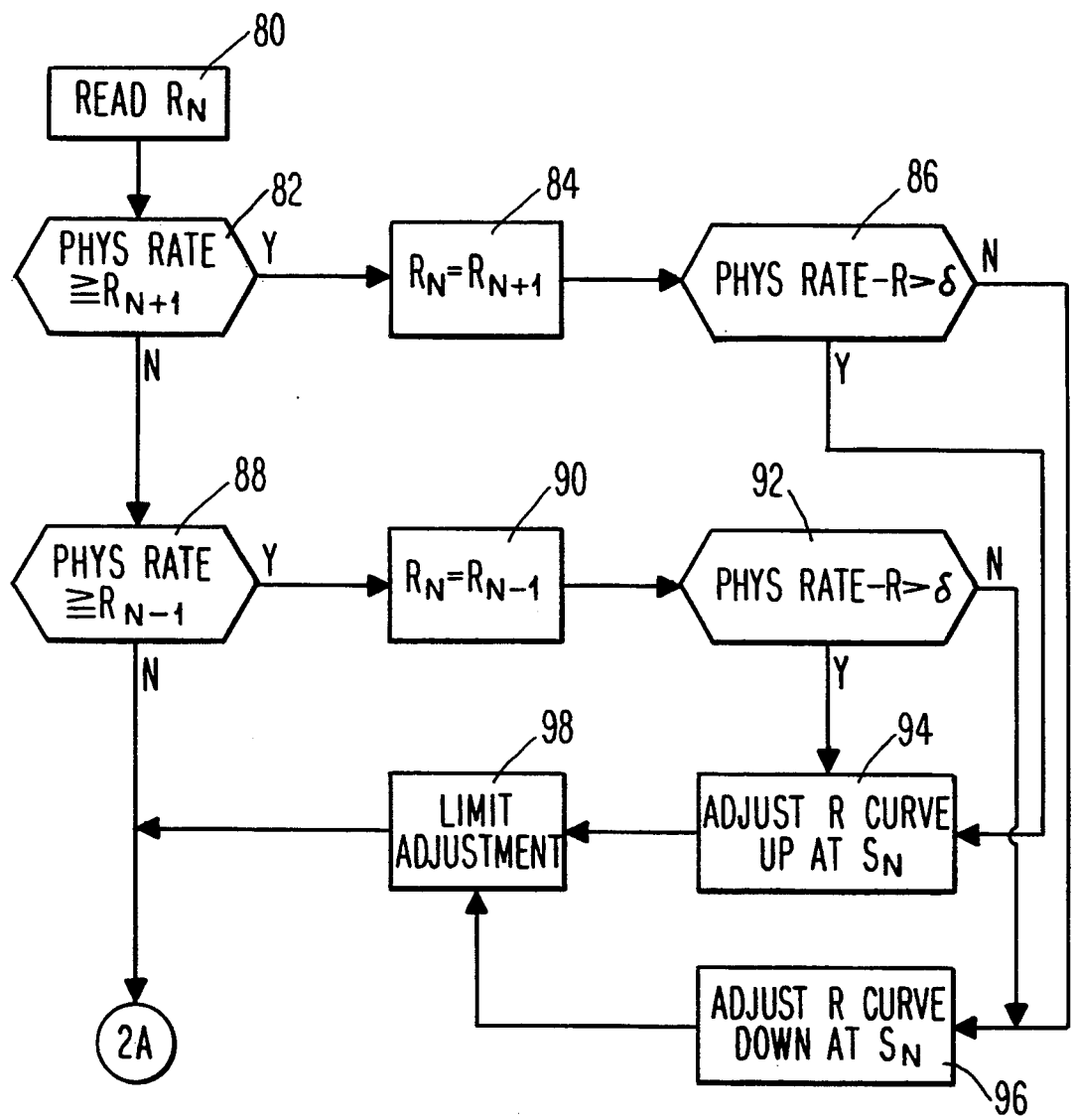
FIG. 4 is a flow diagram of another embodiment of the pacemaker of this invention wherein rate response function adaptations are made by comparisons between sinus rate and sensor-indicated rate at a plurality of sinus rates within the pacemaker pacing range.

Referring now to FIGS. 3 and 4, there is shown another embodiment of this invention for providing adjustments or adaptation to the rate response function at rates other than UPL, i.e., substantially throughout the pacing range available to the pacemaker. Referring to FIG. 3, there are shown curves of decision rates versus phys rate. The lower line, designated DPR, represents the dynamic pacing rate. DPR represents the rate at which the pacemaker is set to deliver paces as a function of sensed phys rate, which is a measure of physiological atrial rate. See the referenced U.S. Pat. No. 5,247,930. Thus, as indicated, DPR is set at a lower limit (LPL) for all sensed rates up to a certain point, after which DPR increases linearly with phys rate. When the sensor calls for a higher or lower rate, the horizontal portion of the DPR curve moves up or down, as indicated by the arrows. The decision curve marked DTL, for dynamic tracking limit, represents the upper limit of the tracking range, i.e., the range within which sensed atrial pulses are tracked for generation of synchronized ventricular stimulus pulses. UPL is shown as the upper pacing limit, and represents a programmed upper limit beyond which rate the pacemaker will not generate and deliver stimulus pulses. Also indicated schematically are arbitrary rates $R_1, R_2 \ldots R_N$ representing rates between the lower pacing limit and the upper pacing limit. These rates are utilized in the flow diagram of FIG. 4.

Referring now to FIG. 4, in this embodiment of the invention, the routine first reads $R_N$ at block 80. $R_N$ represents the last one of the selected rates $R_1$ through $R_N$, through which the phys rate has moved in either an upward or a downward direction. At step 82, phys rate is compared to see whether it is equal to or greater than $R_{N+1}$. If yes, meaning that the phys rate has increased beyond the next selected $R_N$, $R_N$ is incremented at block 84. Following this, at step 86, the phys rate is compared to the sensor rate R, to determine whether the difference is greater than an arbitrarily determined amount delta. If yes, meaning that R has not followed as closely as delta to phys rate, the routine branches to block 94, where the R curve is adjusted upward at $S_N$ (the sensor value corresponding to $R_N$). In other words, at block 94, the value of R corresponding to $S_N$ is increased by one step, making the rate response more aggressive. Returning to 86, if the comparison results in a no response, the routine branches to block 96, where the R curve is adjusted downward, or made less aggressive, at $S_N$.

Returning to block 82, if the comparison results in a no response, the routine branches to block 88 where it determines whether phys rate is equal to or less than $R_{N-1}$. If yes, the routine branches to block 90, where $R_N$ is set equal to $R_{N-1}$. Following this, the routine goes to block 92 where Phys Rate−R is measured and compared to see if it is greater than delta. If the answer is yes, the routine branches to block 94, where the R curve is adjusted upward at $R_N$. If the answer is no, the routine branches to block 96, where the R curve is adjusted downward at $R_N$.

Following either adjustment at block 94 and 96, the routine goes to block 98, where a limitation is set on the next adjustment. This limitation is the same as the prevent step of blocks 68 and 78 in FIGS. 2A and 2B, and limits any further change in the curve at this phys rate for a predetermined amount of time. Following either block 88 or 98, the routine branches to 2A, which is the routine of FIG. 2A, discussed above.

The algorithm for adjusting the response curve may be simple or complex, within the scope of this invention. Thus, if an adjustment is made at $R_N$, the entire response function (or curve) may be re-calculated based upon the prior values for LRL and URL and the new S/R relation at $S_N$, making certain that R increases monotonically with values of S that indicate a higher pacing rate. In any event, when the value of R is changed at any point, the routine should check to see that values of R corresponding to higher and lower S values are properly set to greater and lower values.

As noted above, for a VDDR pacemaker it is assumed that the sinus rate is reliable. In order to safeguard against a situation where the sinus rate becomes unreliable after implantation, it is necessary to provide that the sinus-tracking feature of this invention can be disabled or bypassed if necessary. If the attending physician observes a condition such as chronotropic incompetence, the tracking feature of this invention can be disabled by appropriate programming. Such programming would suitably involve disabling the negative sinus rate controlled adaptation, and initiating an automatic positive adaptation every eight days, which can be done through programmer 51. Alternately, the pacemaker incorporates logic for recording when the natural sinus does not respond to the onset of exercise properly. For example, by using an activity-based sensor which reliably indicates exercise episodes, and comparing the sensor indications with sinus rate during such episodes, it can be determined whether the sinus rate is reliable. If it is found to be unreliable, then the routines of FIG. 2A and/or FIG. 4 are disabled.

We claim:

1. (Amended). A rate responsive demand pacemaker having a pulse generator for generating and delivering stimulus pulses, rate sense means for sensing natural beats and obtaining a measure of the rate of said natural beats, a rate control for controlling the rate of delivery of stimulus pulses by said pulse generator, rate responsive means for obtaining sensor signals indicative of desired pacing rate and for generating therefrom sensor rate signals (R) in accordance with a rate response function which is a function of said sensor signals over a desired pacing range, said rate control circuit controlling said rate of delivery in accordance with R, characterized by first comparing means for comparing said measure of said natural beat rate and R at a predetermined rate, and adjust means operative during detection of natural beats for adjusting said rate response function as a function of said first comparison.

2. The pacemaker as described in claim 1, further comprising limit means for limiting said adjusting.

3. The pacemaker as described in claim 1, wherein said adjust means comprises rate adjust means for adjusting the slope of said rate response at said predetermined rate.

4. The pacemaker as described in claim 1, wherein said pacemaker has mode means for operating in the VDD mode.

5. The pacemaker as described in claim 1, comprising means for setting an upper pacing limit (UPL), and wherein said first comparing means has initiating means for initiating said comparison when said natural rate equals said UPL.

6. The pacemaker as described in claim 5, having means for setting a first predetermined increment, and wherein said first comparing means comprises first determining means for determining whether said sensor rate (R) is less than UPL by more than said first predetermined increment, and first changing means for changing said rate response function so that R reaches UPL more aggressively when said sensor rate (R) is less than UPL by more than said increment.

7. The pacemaker as described in claim 6, comprising limit means for limiting said changing means to change said rate response only once per day.

8. The pacemaker as described in claim 6, having means for setting a second predetermined increment, and wherein said first comparing means comprises second determining means for determining when the difference between UPL and the sensor rate is less than said second predetermined increment, and second changing means for changing said rate response function to be less aggressive when said difference is less than said second predetermined increment.

9. The pacemaker as described in claim 1, comprising means for setting an upper pacing limit (UPL), and further comprising second comparing means operative following delivery of pacing pulses for determining when the pacing rate is equal to or greater than a predetermined UPL, combined with means operative when the pacemaker pacing and when the pacing rate is determined to be equal to or greater than UPL for determining if said rate response is too aggressive and for reducing the aggressiveness of said rate response if it is determined to be too aggressive.

10. The pacemaker as described in claim 9, further comprising means for setting a rate below UPL, and intermediate comparing means for comparing said measure of the rate of sensed heartbeats with R when said measure is at about said rate below UPL, and intermediate change means for changing said rate response as a function of said intermediate comparison.

11. The pacemaker as described in claim 10, comprises means for setting a plurality of predetermined rates below UPL, and wherein said intermediate comparison means comprises means for comparing the measure of sensed natural rate with R when said measure is at about one of said plurality of rates, and means for adjusting said rate response as a function of each said comparison.

12. A pacemaker having a pulse generator for generating and delivering stimulus pulses, rate sense means for sensing natural beats and obtaining a measure of the rate of said natural beats, a rate control for controlling the rate of delivery of stimulus pulses by said pulse generator, rate responsive means for obtaining sensor signals indicative of desired pacing rate and for generating therefrom sensor rate signals (R) in accordance with a rate response function which is a function of said sensor signals over a desired pacing range, said rate control controlling said stimulus pulse rate as a function of R in the absence of sensed natural beats, further comprising rate response adjust means for automatically adjusting said rate response function as a function of said rate measure so as to track said rate measure, and means for limiting said adjusting.

13. The pacemaker as described in claim 12, comprising means for setting an upper pacing limit (UPL), means for determining when said rate measure is at said UPL, and said adjust means having means for comparing said rate measure with R when said measure is determined to be at UPL.

14. The pacemaker as described in claim 12, wherein said automatic adjust means comprises means for comparing said measure of rate with the corresponding R at each of a plurality of rates, and for adjusting said rate response function as a function of said comparisons so as to track said rate measure.

15. The pacemaker as described in claim 14, wherein said rate control has means for defining rates through a predetermined range, and wherein said rate response adjust means comprises means for comparing said rate measure with R substantially throughout said range and for adjusting said R response as a function of said comparisons.

16. The pacemaker as described in claim 12, comprising means for determining the presence of cardiac conditions calling for an increased rate, and means for determining when said rate measure does not increase under said cardiac conditions and for inhibiting said adjusting of the rate response function following such a determination.

17. A VDD pacemaker system for pacing a patient, having means for providing an adjustable rate response function, means for providing first criteria and second criteria, rate response means for obtaining sensor signals (S) and determining therefrom pacing rate signals (R) in accordance with said adjustable rate response function, and means for determining a measure of natural atrial rate of the patient, comprising first adjust means for adjusting said rate response function positively when R is lower than said natural rate in accordance with said first criteria, and second adjust means for adjusting said rate response function negatively when R is not below said natural rate in accordance with said second criteria.

18. The pacemaker system as described in claim 17, further comprising means for disabling said second adjust means.

19. The pacemaker system as described in claim 17, further comprising limit means for limiting the frequency of operation of said first and second adjust means.

* * * * *